(12) United States Patent
Payne et al.

(10) Patent No.: US 6,649,212 B2
(45) Date of Patent: Nov. 18, 2003

(54) MODIFIED SILICON-BASED UV ABSORBERS USEFUL IN CROSSLINKABLE POLYSILOXANE COATINGS VIA SOL-GEL POLYMERIZATION

(75) Inventors: Donald N. Payne, Northville, MI (US); Yei-Ping H. Wang, Troy, MI (US)

(73) Assignee: Guardian Industries Corporation, Auburn Hills, MI (US)

( * ) Notice: Subject to any disclaimer, the term of this patent is extended or adjusted under 35 U.S.C. 154(b) by 186 days.

(21) Appl. No.: 09/917,280

(22) Filed: Jul. 30, 2001

(65) Prior Publication Data

US 2003/0020049 A1 Jan. 30, 2003

(51) Int. Cl.$^7$ .................. B05D 5/06; C08G 77/18; F22V 9/06
(52) U.S. Cl. ............... 427/160; 252/589; 525/476; 528/29; 556/436
(58) Field of Search .................. 252/589; 427/160; 525/476; 528/29

(56) References Cited

U.S. PATENT DOCUMENTS

| | | | |
|---|---|---|---|
| 2,773,778 A | * 12/1956 | Hoch et al. ............. 252/589 X |
| 3,160,675 A | * 12/1964 | Kastrop |
| 3,431,129 A | * 3/1969 | Ismail ................... 252/589 X |
| 3,580,927 A | * 5/1971 | Wear ..................... 252/589 X |
| 3,817,924 A | * 6/1974 | Young, Jr. et al. ...... 252/589 X |
| 4,051,161 A | * 9/1977 | Proskow |
| 4,168,332 A | * 9/1979 | Leinen et al. ................ 427/160 |
| 4,235,954 A | * 11/1980 | Humphrey, Jr. ............. 427/160 |
| 4,299,886 A | * 11/1981 | Soejima et al. ......... 427/160 X |
| 4,555,545 A | * 11/1985 | Kimura et al. ............ 528/29 X |
| 4,960,615 A | * 10/1990 | Stout et al. ................. 427/160 |
| 5,192,621 A | * 3/1993 | Gillberg-Laforce et al. 427/160 X |
| 6,497,964 B1 | * 12/2002 | Matsumura et al. ...... 528/29 X |

\* cited by examiner

*Primary Examiner*—Richard D. Lovering
(74) *Attorney, Agent, or Firm*—Nixon & Vanderhye P.C.

(57) ABSTRACT

Functionalized organo-silicone compounds incorporate ultraviolet radiation screening or absorbing moieties. The novel materials of the invention are durable and provide uniform UV absorption properties when used in various applications, including coatings on substrates such as glass, in particular float glass. Methods for their preparation and use are also provided.

7 Claims, 11 Drawing Sheets

MODIFIED SILICON-BASED UV ABSORBERS USEFUL IN CROSSLINKABLE POLYSILOXANE COATINGS VIA SOL-GEL POLYMERIZATION

FIELD OF THE INVENTION

This invention is related to novel ultraviolet (UV) radiation-absorbing organo-silicone ester and ether molecules, in both monomeric and polymeric forms. Preferred methods for their production from silicone hydrides and organic UV absorbers and usage in coatings prepared via acid catalyzed alkoxysilane sol-gel synthesis on various glass (soda-lime, etc.) substrates are provided. Coatings on glass substrates, incorporating embodiments of the disclosed invention, aid in preventing UV radiation from degrading underlying articles.

BACKGROUND AND SUMMARY OF THE INVENTION

Numerous organic and inorganic compounds that absorb UV radiation have been described in the prior art. As used herein and in the accompanying claim, a UV absorber is defined to mean a compound that absorbs radiation of wavelengths starting in the near visible portion of the electromagnetic spectrum, around 400 nanometers to the so-called vacuum ultraviolet, around 200 nanometers in wavelength. These compounds are often used to protect items underlying transparent, semitransparent and/or translucent substrates from the degradative effects of ultraviolet radiation absorption. Applications include, but are not limited to eyeglasses, windows, and glass panes in paintings, art prints, and the like. UV absorbers coated onto glass for the protection of paintings, pictures, and the like are of particular importance with a view to the present invention.

One class of polymers useful as matrices for UV absorbers are crosslinked polysiloxanes synthesized by sol-gel methods. As used herein and in the accompanying claims, reference to a "sol-gel" synthesis is intended to mean any method of preparation of a poly- or oligo-siloxane using hydrolysis of alkoxysilanes via acid, base, or other useful catalysts, e.g. coordination catalysts, to produce oligomer and/or polymers useful for preparing films and coatings. Polysiloxanes produced via sol-gel synthesis and applied in thin coatings are generally transparent to electromagnetic radiation in the so-called "visible" wavelengths of the electromagnetic spectrum where the human eye absorbs such radiation.

However, it is generally recognized in the sol-gel reaction art that effectively dispersing and retaining organic-base additives such as radiation absorbers, is problematic. Organic UV absorbers are often insoluble in silane/silicone monomers and polymers and can require extensive mixing procedures to produce a uniform, albeit unstable, dispersion useful for various applications. Additionally, with a view to the prior art, monomeric UV absorbers are known to evaporate during heat processing which is required to finally cure siloxane systems. Further, monomeric UV absorbers often exhibit a yellow hue or color when they are not fully dispersed. This color effect can require correction by adding expensive dyes which further complicates the formulation and cost of a UV absorbing coating system. Finally, monomeric UV absorbers tend to both 1.) leach out of polysiloxane matrixes over time and 2.) deactivate via oxidative decomposition.

One potentially useful method of retaining UV absorbers is to covalently bond them onto alkoxysilane monomers for subsequent incorporation into a polysiloxane matrix via sol-gel synthesis. Several chemistries have been utilized in this regard. One modified alkoxysilane useful in the preparation of certain classes of coating solutions is disclosed in U.S. Pat. No. 4,051,161 to Proskow, the entire disclosure of which is hereby incorporated by reference. Proskow discloses several alkoxysilane-benzophenone monomers prepared by reacting an alkoxysilane that contains an epoxide moiety with a hydroxyl group on a hydroxybenzophenone to form an $\alpha$, $\beta$ hydroxy-ether which covalently links the hydroxybenzophenone and the silane. Proskow's invention appears to be limited to monomeric species for incorporation into polymers containing polysilicic acid (e.g. silica) and hydroxylated fluorocopolymer systems. However, there are problems with and disadvantages to directly bonding an alkoxysilane modified UV absorber (e.g. a hydroxybenzophenone) into a sol-gel polymerized matrix as disclosed in Proskow. Without wishing to be bound by a particular theory, it is believed that, when monomers having multiple sets of multiply reactive groups (e.g. multiple trialkoxysilanes groups) are polymerized into a film-forming network, stresses can be generated throughout the forming film. These stresses can cause localized failures in coatings thus leading to premature film oxidation and loss of UV absorbers.

Finally, because of their low viscosity, sol-gel polymerizations often require the addition of so-called "low control agents" to provide an increase in viscosity. These are typically higher molecular weight oligomers that are used for viscosity control during the monomer reaction and curing stages of film preparation. However, it would be desirable to eliminate these materials as they can cause potential negative effects in the ultimate physical properties of cured siloxane films, e.g. hardness.

It is apparent from the foregoing discussion that improvements in the art of siloxane/silane sol-gel polymerizations related to the addition of functional additives are desirable. Those desirable improvements include, but are not limited to: (a.) the ability to uniformly incorporate organic-base UV absorbers into a silane matrix without reliance on variable mixing schemes and complicated preparation procedures, (b.) the elimination of additional colorants, (c.) minimizing or eliminating the addition of flow control agents, (d.) minimizing possible mechanical stresses in cured films, and (e.) minimizing the loss of additives, such as UV absorbers, caused by processing heat and environmental degradation. It is a purpose of the present invention to fulfill any and/or all of these needs as will be apparent from the following detailed disclosure of this invention.

It is therefore one objective of the present invention to provide UV absorbers which can be uniformly incorporated into polysiloxanes, prepared by sol-gel reactions, to produce films and coatings having uniform radiation absorption characteristics.

It is another objective of the present invention to provide UV screening monomers, macromers and polymers that resist volatilization and decomposition in curable compositions of alkoxysilane monomers.

It is an additional objective of the present invention to provide UV screening monomers, macromers, and polymers which will exhibit low color in polysiloxane films curable on transparent, semitransparent, or translucent substrates.

It is an additional objective of the invention to provide UV absorbing monomers, oligomers, and polymers that display behavior as flow control agents.

It is an additional objective of the invention to provide benzophenoxy-alkoxysilane monomers that are capable of hydrolyzing into polymerizible silanols and unbound hydroxy-benzophenones when utilized in a silane based sol-gel polymerization.

An additional objective of the invention is to provide alkoxysilane based film-forming solutions that are curable onto a substrate and will yield substantially insoluble polysiloxane films having uniform UV absorption characteristics.

It a further objective of the invention to provide methods of preparing and using the disclosed molecules, macromers, polymers and coating compositions.

These and other objectives are exemplified by certain non-limiting embodiments of the invention as disclosed in the following examples and descriptions.

BRIEF DESCRIPTION OF THE DRAWINGS

Reference will hereinafter be made to the drawings, wherein like reference numerals throughout the various FIGURES denote like elements, and wherein.

DETAILED DESCRIPTION OF THE INVENTION

In view of the preceding objectives and/or needs in the art of UV absorbing compounds and coating compositions prepared via sol-gel polymerization, the present invention comprises:

A first embodiment comprising a di-epoxy-silane or di-epoxy-siloxane monomer prepared by reacting a vinyl terminated group also having an epoxy moiety with a dihydridosilane or dihydrido siloxane via a platinum hydrosylation catalyst to yield a di-epoxy silane or di-epoxy siloxane wherein the silicon-containing moiety may or may not further include reactive organic alkoxides. Especially preferred organic alkoxides include, methyl, ethyl and propyl alkoxides. Siloxanes having at least 1 to about 10 Si—O—Si repeat units are preferred. An especially preferred embodiment is di-epoxy-siloxane monomers comprising about four or five siloxane repeat units, and at least one reactive organo-alkoxide wherein the organic alkoxide is methyl or ethyl-alkoxide. A preferred vinyl terminated organic group or compound also having an epoxy group is 3-glycidoxy-1-propylene.

A second preferred embodiment comprises a condensation product of a di-epoxy-silane or di-epoxy-siloxane monomer with an aromatic UV absorber molecules having at least two aromatic hydroxyl groups reactive with epoxide groups. The reaction can be run to prepare a high polymer or produce dimer, trimer, tetramer or other higher -mer condensation products. The condensation product contains both UV absorbing repeat units and alkoxy-siloxane and/or silane repeat units. In a preferred embodiment, an oligomer is produced having from about 2 to 10 repeat units of the basic structure (e.g. hydroxy-benzophenone and siloxane groups covalently bonded) and has a number average molecular weight, $MW_n$, of about 3000 to 4000 grams per mole. Still another preferred embodiment comprises siloxane repeat units having at least one organic alkoxide unit per siloxane repeat unit wherein the alkoxide is ethoxy and/or methoxy groups.

A third preferred embodiment comprises the reaction product of a (multi)-hydroxy-benzophenone or a phenoxy-salt form with respectively a di-or tri-functional alkoxysilane or chloroalkoxysilane to form a hydroxybenzophenone-substituted alkoxysilane ether wherein the hydroxybenzophenone is attached to the silicon atom of the silane through an ether oxygen. In a preferred embodiment, the hydroxybenzophenone is or 2,2' dihydroxy-benzophenone and the alkoxysilane is trimethoxymethylsilane or triethoxymethylsilane.

A fourth preferred embodiment comprises a mixture of substituted alkoxysilanes and a hydroxybenzophenone-substituted alkoxysilane (HBAS) useful in sol-gel polymerizations initiated by acid or base or other suitable catalyst. In a preferred embodiment the alkoxysilanes are methyltriethoxysilane and phenyltriethoxysilane in a 1 to 1 molar ratio and the HBAS is a disubstituted hydroxybenzophenone bonded through hydroxyl oxygen, (thereby forming an ether linkage) to a methyltriethoxysilane.

A fifth preferred embodiment comprises a film forming composition for an acidic sol-gel polymerized film comprised of substituted alkoxysilanes and a poly(hydroxybenzophenone-alkoxysiloxane). In an especially preferred embodiment, the substituted alkoxysilanes are a mixture of methyltriethoxysilane and phenyltriethoxysilane, and the polymer formed has a number average molecular weight, $MW_n$ of about from 3000 to 4000 grams per mole.

A sixth preferred embodiment comprises a film-forming mixture of alkoxysilane monomers, hydroxybenzophenone-substituted alkoxysilanes, and a hydroxybenzophenone-alkoxy and/or alkyl-silane co-polymer useful for forming a substantially transparent polysiloxane film that efficiently absorbs UV radiation.

These and other embodiments are disclosed in the following nonlimiting Examples.

EXAMPLES

Example 1

Preparation of a di-epoxy-monosiloxane Monomer

Figure 1:
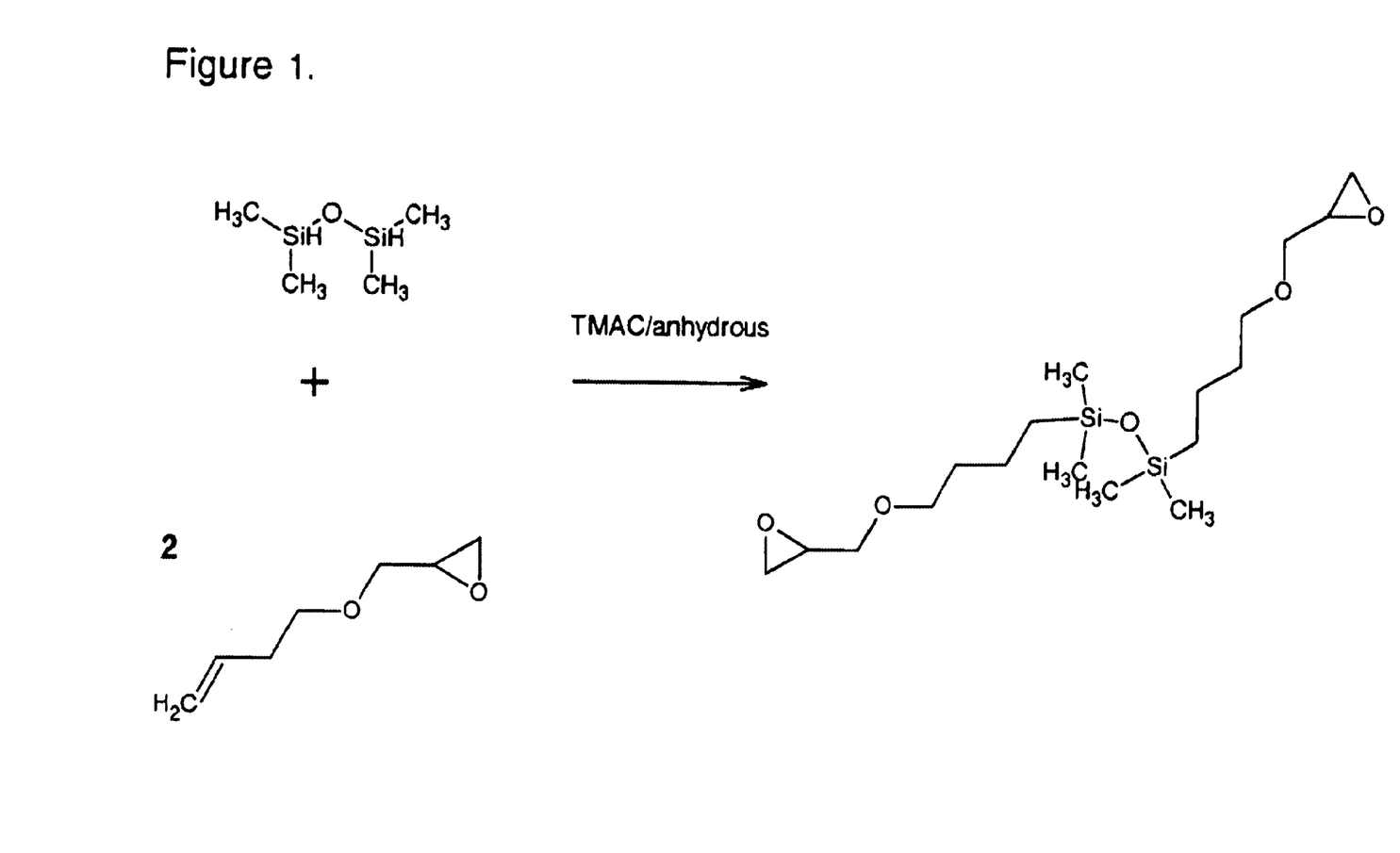
FIG. 1 is representation of the structure of one of the embodiments of diepoxy-siloxane monomers whose synthesis is disclosed in Example 1 which is useful in preparing UV-absorbing siloxane/silane compounds.

Anhydrous, dry tetramethyldihydrido siloxane, ((CH$_3$)$_2$HSi—O—Si(CH$_3$)$_2$H), available from United Chemical Technologies Inc, 2713 Bartram Road Bristol, Pa. 19007 or Sigma-Aldrich Chemical, PO Box 355, Milwaukee, Wis. 53201 is mixed at a molar ratio of at least 1:2 with a solution of allylglycidylether (or other sufficient quantity to ensure that a di-epoxysiloxane monomer is produced) in a nonreactive solvent. These compounds are reacted using a platinum catalyst system, such as platinum dispersed in an inert carrier solvent or a platinum compound such as chloroplatinic acid, over a temperature range of from about 30° C. to about 100° C., most typically about 50° C., to yield a di-epoxy-terminated siloxane monomer. Other useful catalysts and reaction conditions are described in U.S. Pat. No. 2,946,701 to Plueddemann, issued Jul. 26, 1960, the entire disclosure being hereby incorporated by reference. This reaction and product are illustrated in FIG. 1.

Example 2

Figure 2:
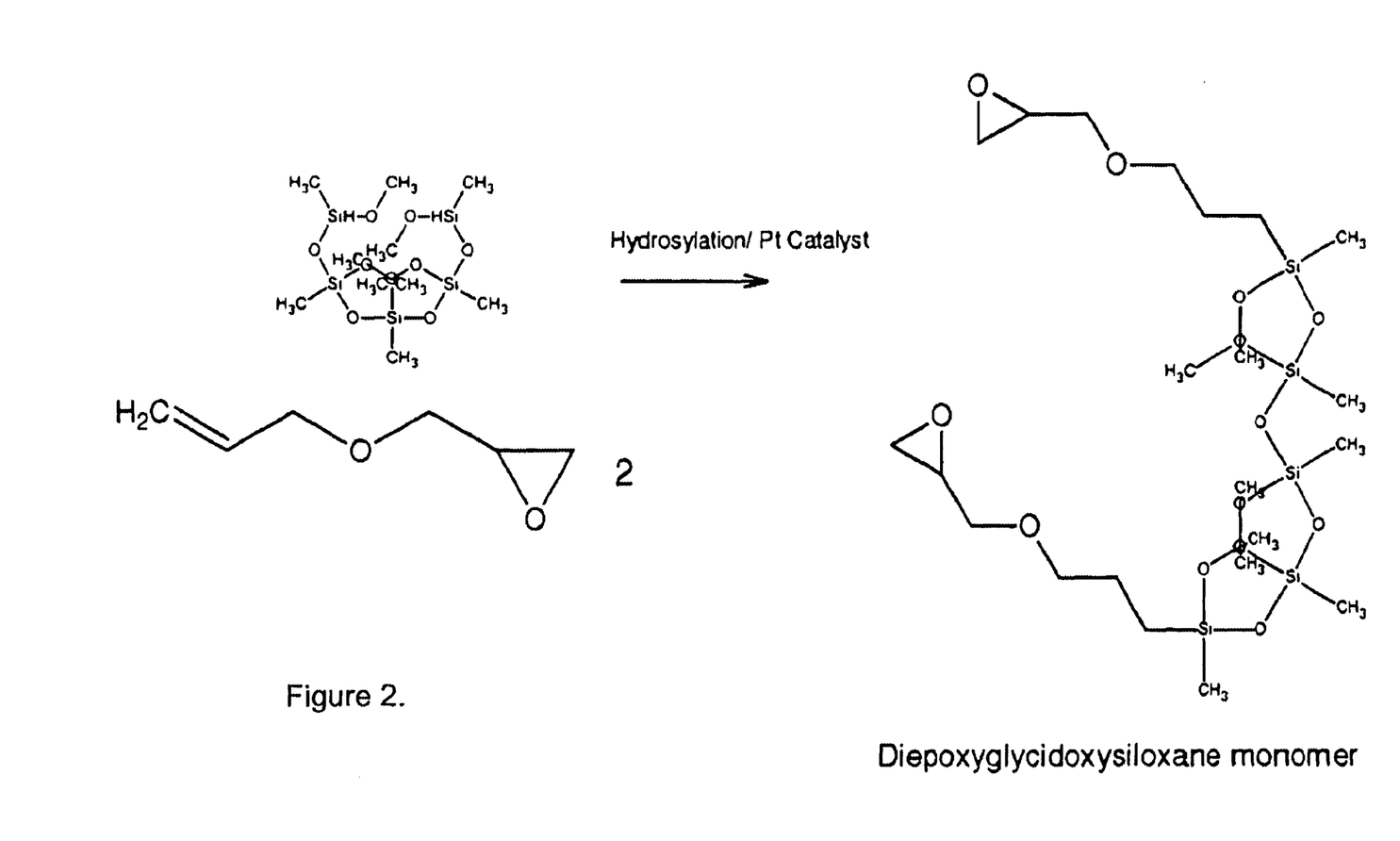
FIG. 2 is a representation of one of the embodiments of diepoxy-terminated alkoxy-siloxane monomers produced by the reaction scheme of Example 2 useful in preparing UV-absorbing siloxane compounds.

Preparation of a di-epoxy Siloxane Macromer Having Reactive Alkoxide Groups An anhydrous solution of a siloxane oligomer having a molecular weight of ca. 438 grams per mole and the molecular formula $C_{11}H_{34}O_4Si_5$ having a reactive hydrogen atom bonded on two Silicon atoms is mixed at a molar ratio of 1:2 with a dry solution of allylglycidylether so that there are two ethers per siloxane molecule available for reaction. The siloxane is available from United Chemical Technologies Inc, 2713 Bartram Road Bristol, Pa. 19007. The reagents are reacted using a platinum catalyst system such as platinum dispersed in an inert carrier solvent or a platinum compound such as chloroplatinic acid at a temperature of about 50° C. A di-epoxide terminated alkoxy functional siloxane is produced. FIG. 2. is a representation of a reaction scheme useful to produce embodiments of the above.

Example 3

Poly-(hydroxybenzophenone-co-diepoxy Alkoxysilane)

Figure 3:
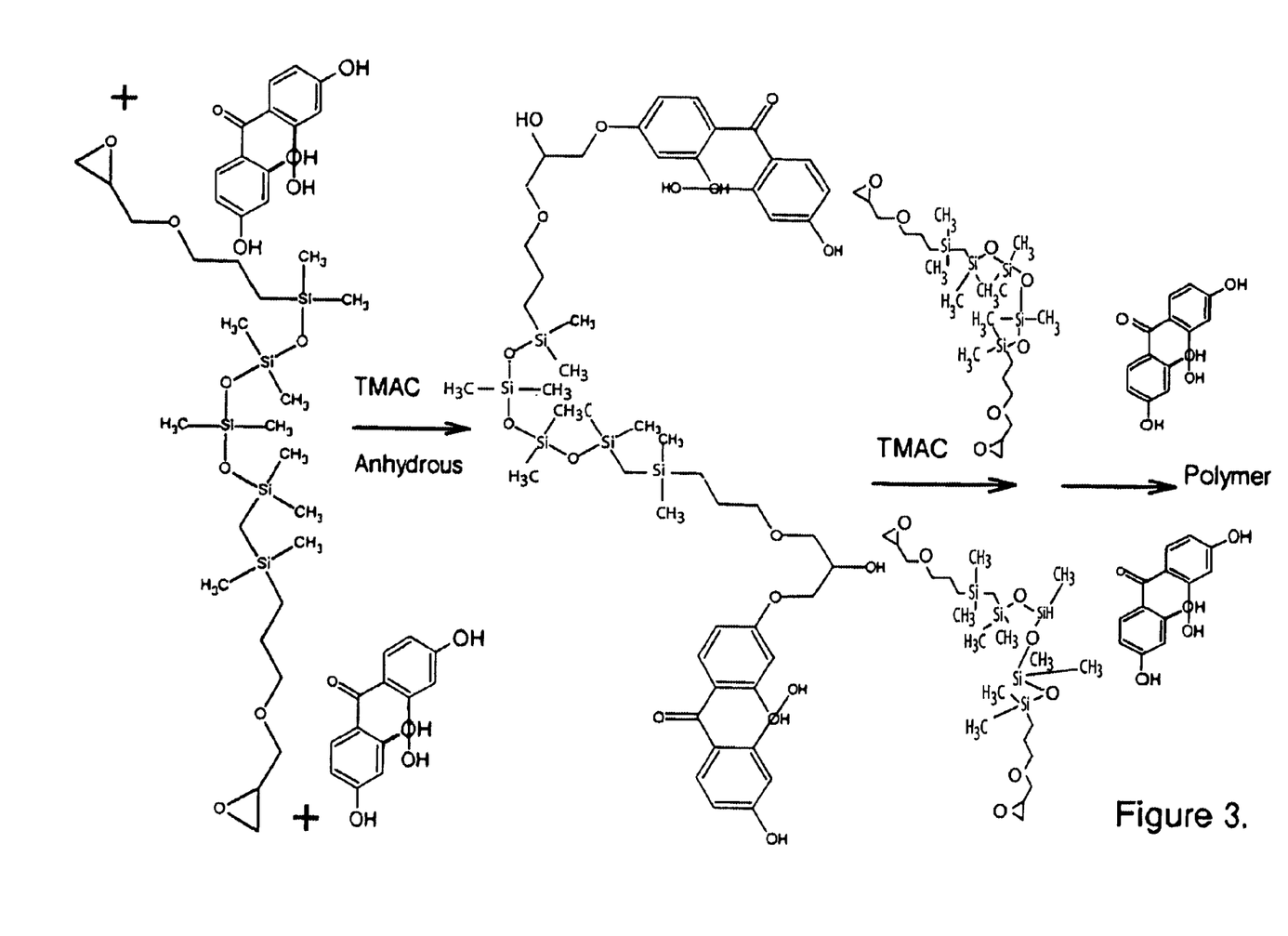
FIG. 3 is a reaction scheme to produce one of the embodiments of a hydroxybenzophenone-epoxy siloxane polymer disclosed in Example 3. which can be used as an ultraviolet radiation absorbing material and/or as part of a curable film forming composition which absorbs ultraviolet radiation.
Figure 4:
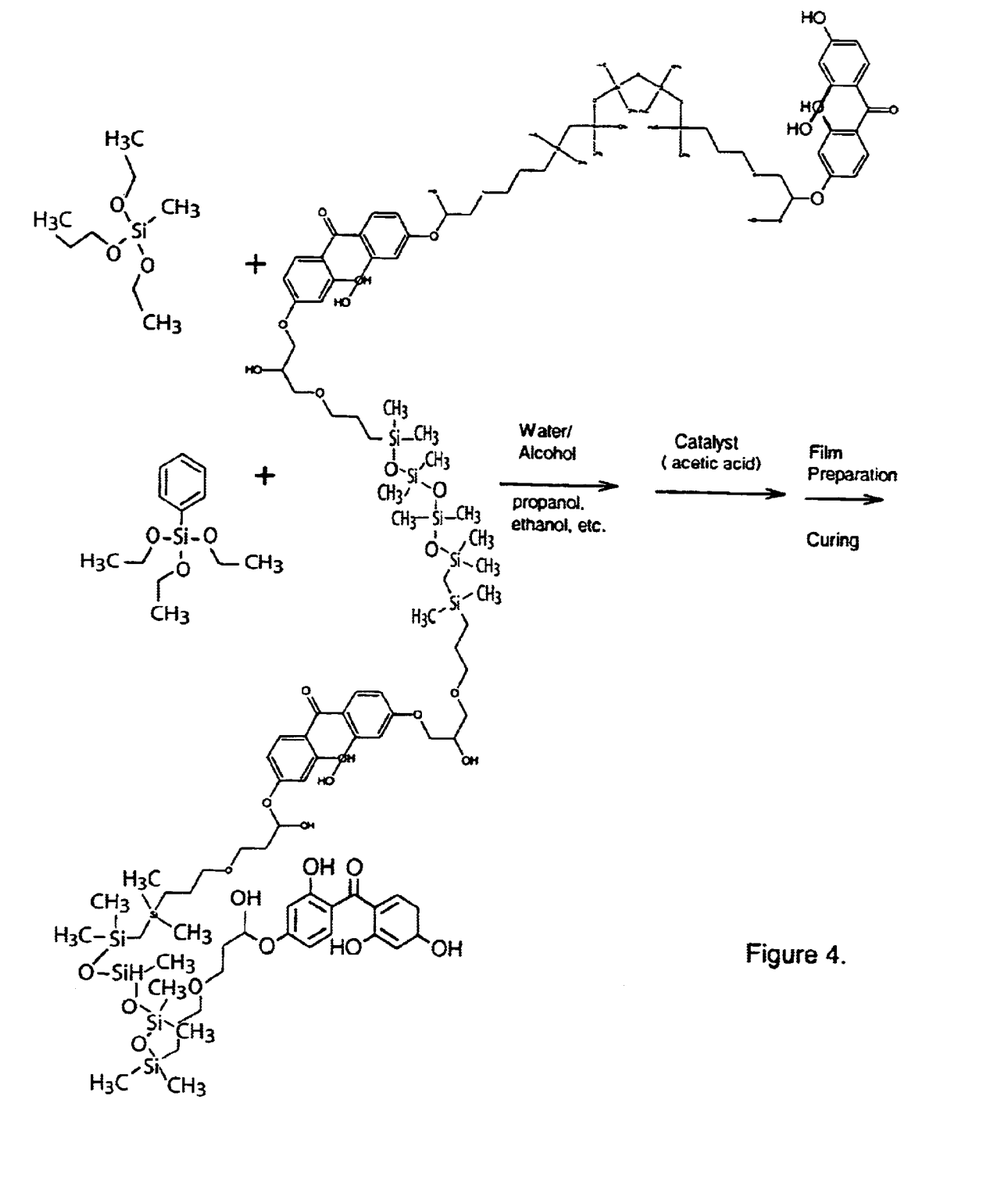
FIG. 4 is a representation of a reaction scheme useful to produce embodiments of films incorporating poly(hydroxybenzophenone-co-diepoxy alkoxysilanes) (as disclosed in Example 3.) with additional organo silane monomers.

A di-epoxysiloxane from either Example 1 or 2 or both is reacted with a multifunctional functional aromatic hydroxyl-containing UV screening moiety under anhydrous conditions in the presence of a quaternary ammonium catalyst such as tetramethylammonium chloride; for example, a tetrahydroxy-benzophenone wherein the 4' and 2'hydroxyl groups are both reactive such as 2,2', 4,4' tetrahydroxybenzophenone as disclosed in U.S. Pat. No. 4,051,161, issued Sep. 27, 1977 to Proskow and assigned to E. I. Dupont de Nemours and Company, the entire disclosure of which being incorporated by reference. A reaction will occur between the hydroxyl- and epoxide groups to form an alpha-beta hydroxy ether having alternating hydroxybenzophenone and di-epoxy-alkoxysilane moieties (i.e. a polymerization). Depending on the temperature chosen, the reaction is run from 2 to 10 hours, preferably 4 to 8 hours. The mixture changes into homogeneous, viscous oil on reacting. FIG. 3. illustrates this reaction scheme.

Example 4

Sol-Gel Films Prepared From Alkoxysilane Monomers and Poly (hydroxybenzophenone-co-diepoxy Alkoxysilane) Oligomers from Example 3

About 3 grams of an oligomer prepared by the method of Example 3., having a number average molecular weight, $MN_n$, of about 3400 g/mol is mixed into 10 grams of butanol and about 35 mls of propanol along with one gram of phenyltriethoxysilane and one gram of methyl triethoxysilane and sufficient water. The mixture is heated to about 50 degrees Centigrade until all the oligomer dissolves and the solution is uniform. The catalyst in the form of acetic acid, about 0.15 mls, is mixed into the solution in the form of a alcoholic mixture. The reaction of the silanes and the oligomer is allowed to run for between 4 and 12 hours as required by the final film properties desired.

The reacted mixture is cast as a film on a cleaned, dry float glass substrate by coating to thickness using a doctor blade. The coated substrate is allowed to equilibrate in air prior to oven drying. The coated substrate is then dried in a heated oven at about 200–250 degrees for several hours to produce a hard, tack free, transparent film. During drying no visual indications of evaporation of benzophenone is apparent i.e. there are no yellow vapors given off as with formulations containing unbonded benzophenones.

Figure 5:
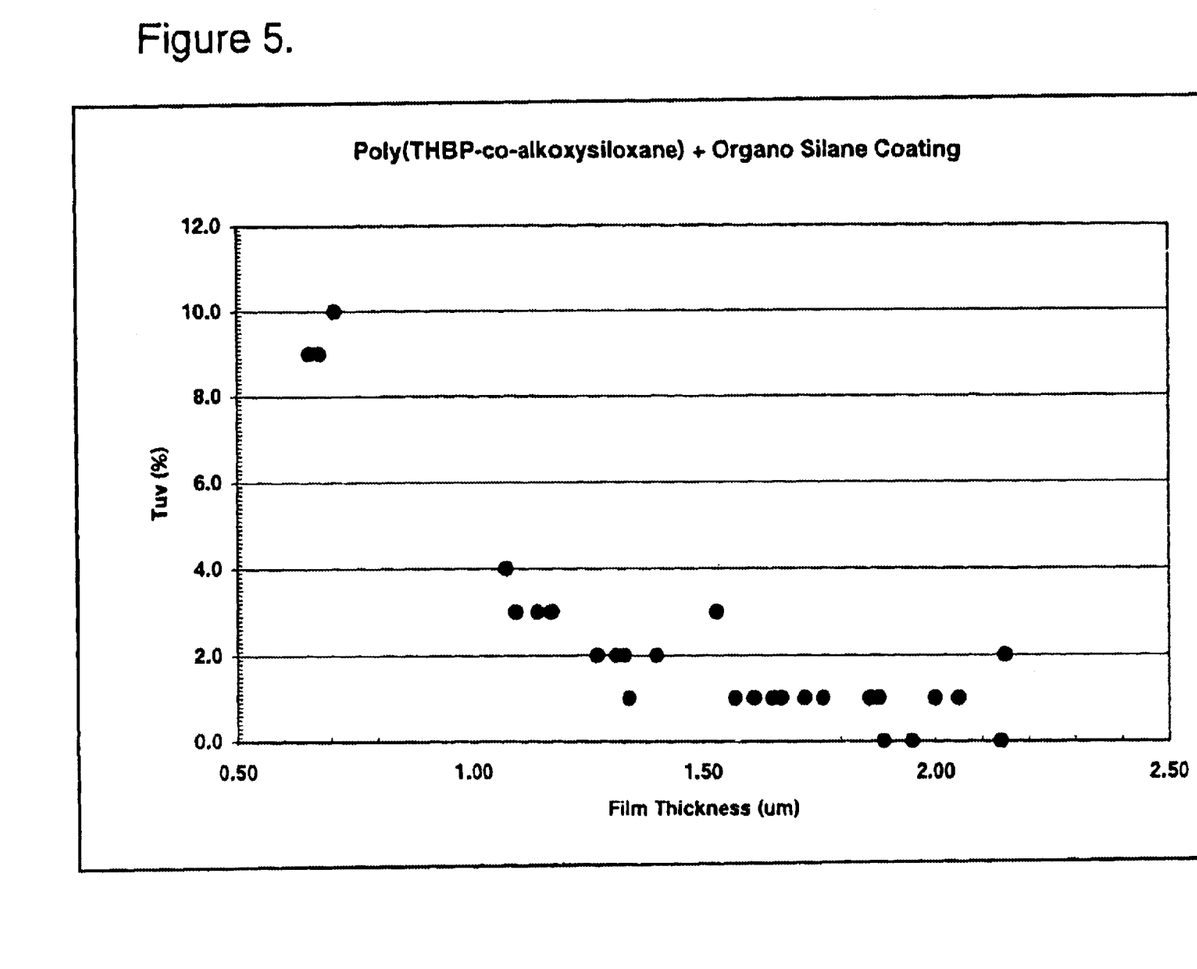
FIG. 5 is a graphical representation of the total UV radiation absorption/transmission properties of the film produced according to the reaction and preparation scheme of FIG. 4.

The film is tested for total ultraviolet radiation transmission, % Tu,v and found to display uniform UV absorption with concentration: monotonic with concentration. FIG. 5 displays the expected results.

Example 5

Figure 6A:
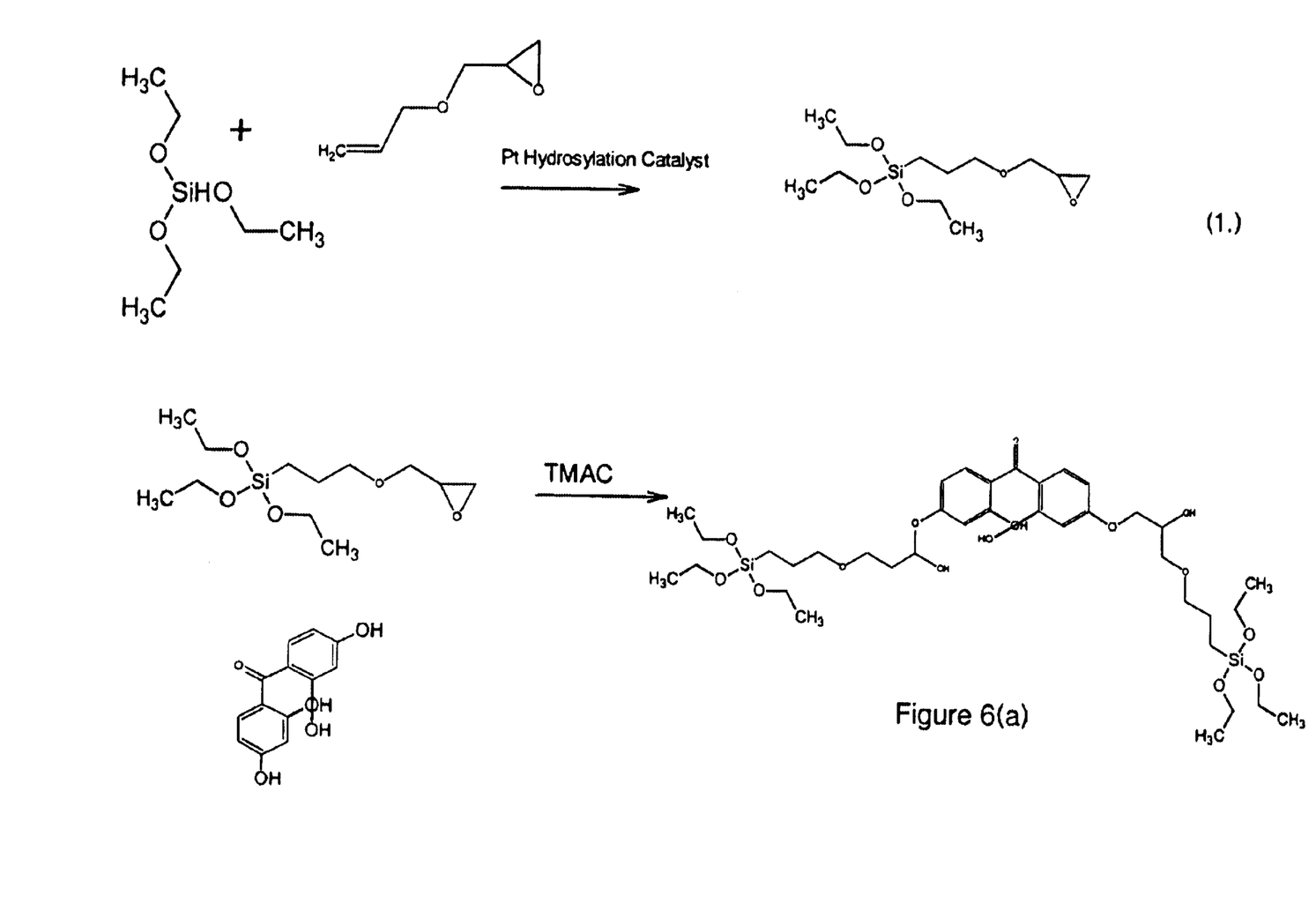
FIGS. 6(a) and (b) are representations of reaction schemes useful to produce embodiments of the alkoxy benzophenones disclosed in Example 5.
Figure 6B:
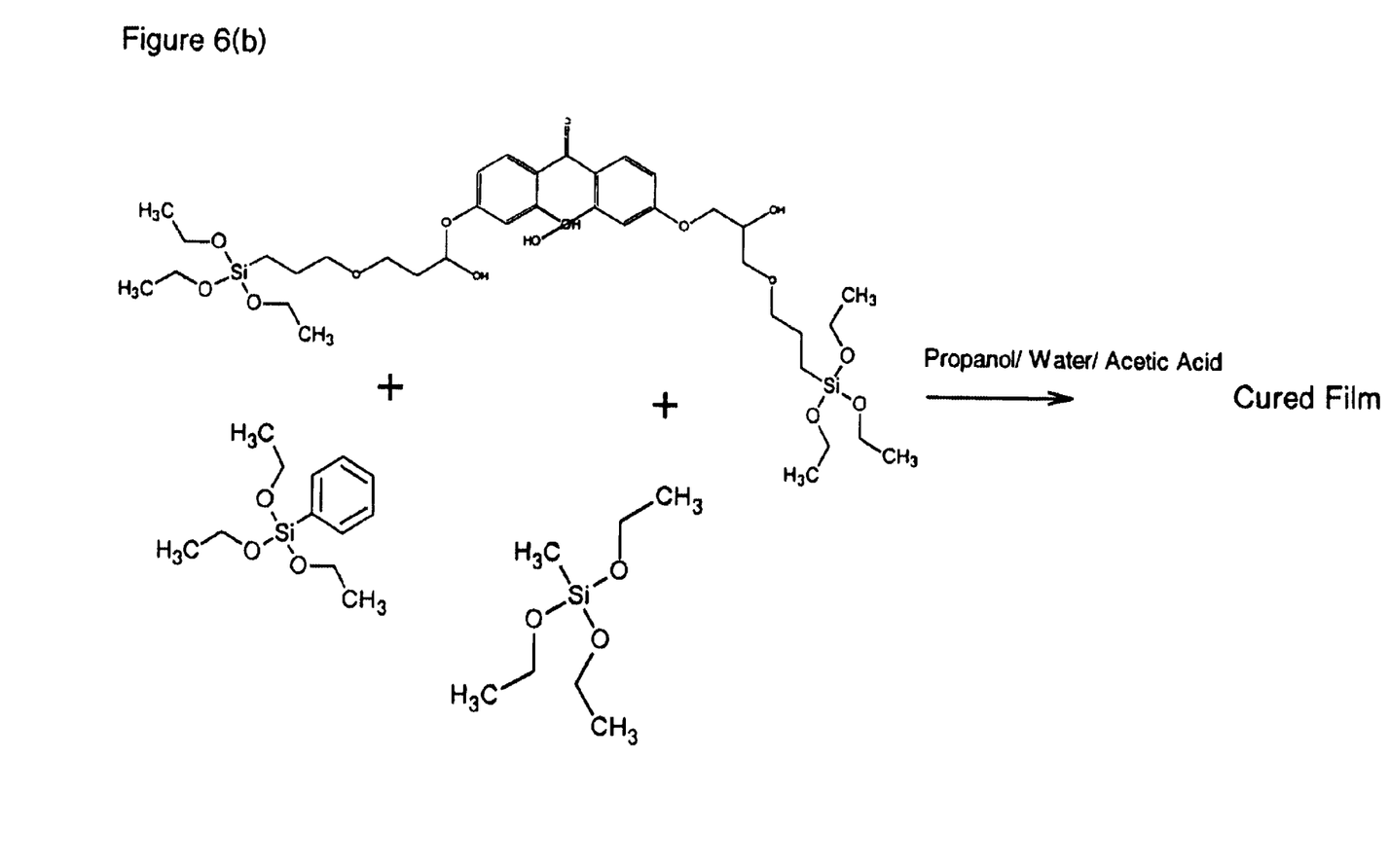
Figure 7:
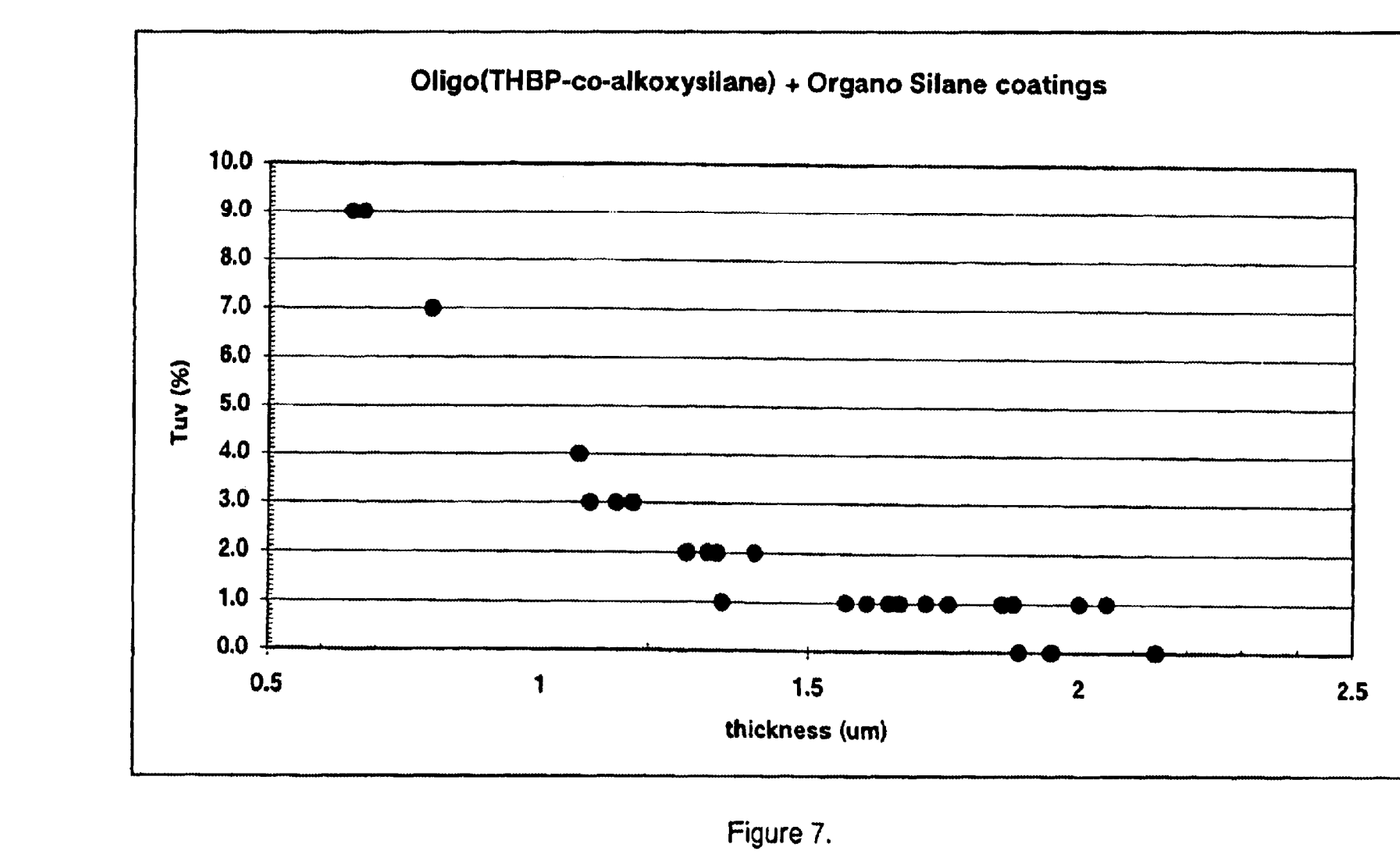
FIG. 7 is a representation of the expected UV absorption characteristics of a sol-gel polymerized film prepared according to the reaction scheme in Example 5. and according to FIG. 6.(b) from Example 5.

Preparation of Films From Tetrahydroxybenzophenone/γ-Glycidoxypropyltrimethoxysilane, Phenyltriethoxysilane and Methyltriethoxysilane Using Acetic Acid Catalyst A coating solution is prepared using the method in Example 2 in U.S. Pat. No. 4,051,161-"2,2',4,4'-Tetrahydroxybenzophenone/γ-Glycidoxypropyltrimethoxysilane 1:2 Adduct". The resulting oil is mixed with the ratio of phenyl and methyl trimethoxysilane monomers used in Example 4 above. The reaction scheme is shown in FIGS. 6.(a) and (b). A flow control agent (BYK 375) is optional and is useful at levels up to about 3 weight percent of the total mixture. Films are prepared in the same manner as in Example 4, above. A transparent, hard film is produced. The film has UV absorption characteristics according to FIG. 7.

Example 6

Figure 8A:
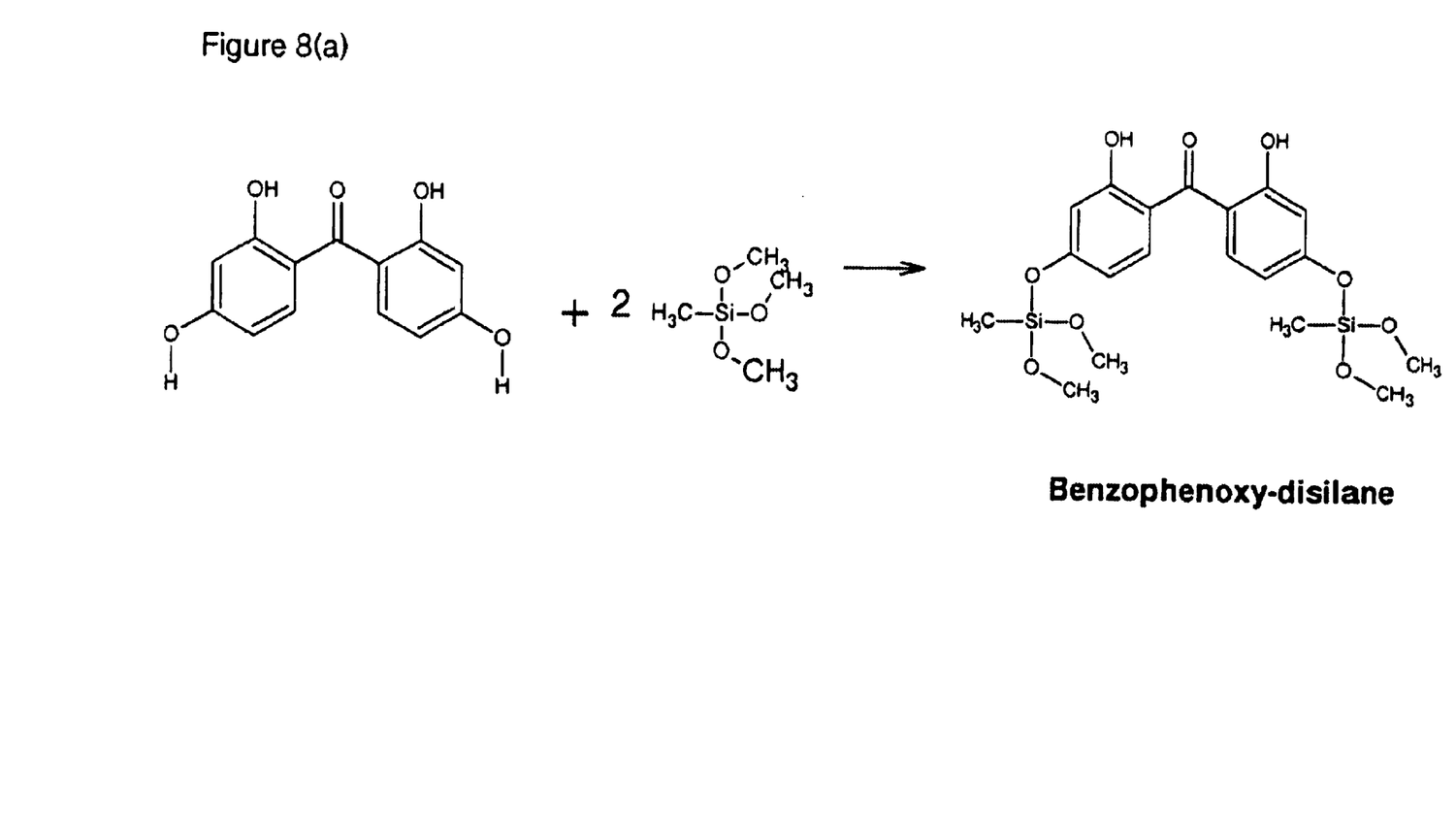
FIGS. 8(a) and (b) are representations of reaction schemes useful to prepare embodiments of the alkoxysilane-phenoxy benzophenone monomers as disclosed in Example 6.

Preparation of 2,2' di-(dimethoxymethylsilyoxy), 4,4'dihydroxy Benzophenone Hydrolysable Monomers Synthesis I: A solution of tetrahydroxybenzophenone (Aldrich Chemical) is treated with sufficient caustic, i.e. sodium hydroxide, to prepare a disodium phenolate salt. This salt solution is mixed at a two to one molar ratio with dichloromethylmethoxysilane (Aldrich, United Chemicals) to yield 2,2' di-(dimethoxymethylsilyoxy), 4,4'dihydroxy-benzophenone having the structure shown in FIG. 8(a).

Figure 8B:
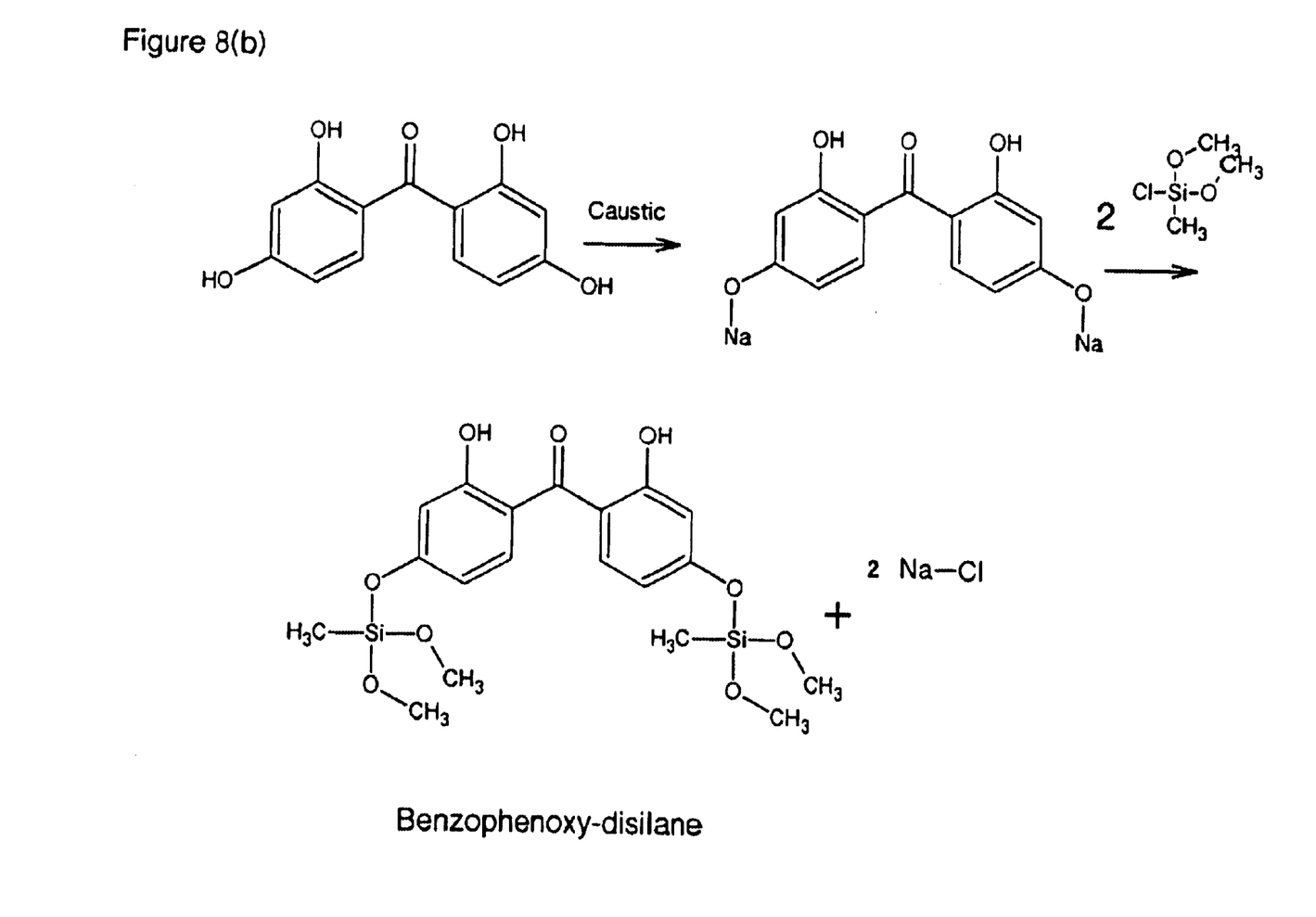
Figure 9:
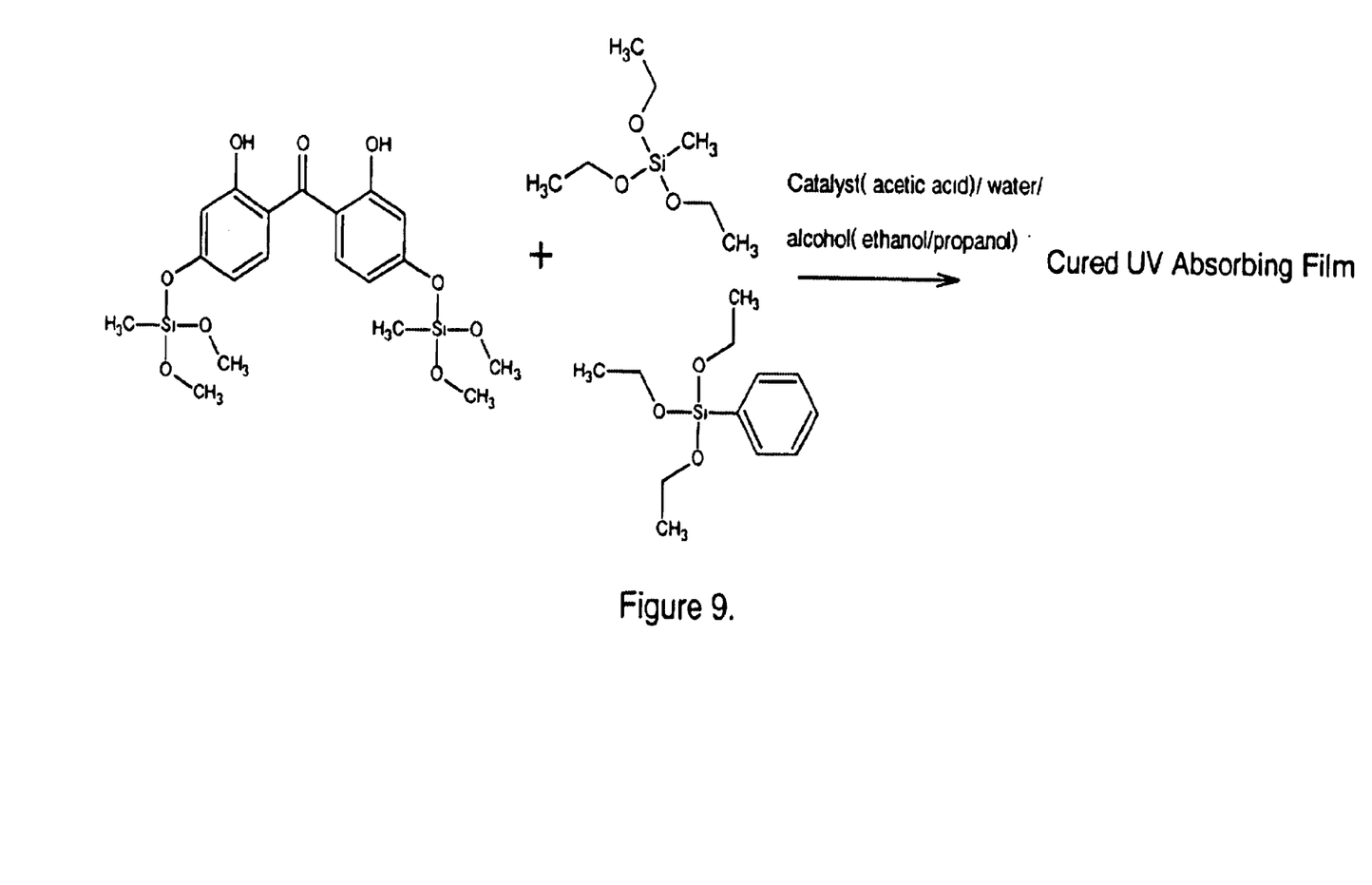
FIG. 9 is a representation of a reaction scheme useful to prepare an alkoxysilane-based sol-gel film incorporating embodiments of the phenoxybenzophenone monomers disclosed in Example 6. and in FIG. 8.

Synthesis II: A solution of tetrahydroxybenzophenone is added along with a portion of trimethoxymethylsilane at a molar ratio of two to one. Introducing caustic soda and heating the system accomplishes the transesterification. The isolation is carried out via vacuum distillation, or fractional crystallization, from a mixture of solvents such as benzene and/or hydrocarbons such as heptane. FIG. 8(b) shows the reaction scheme useful to produce embodiments of the disclosed invention.

Example 7

UV Absorbing Coating Incorporating 2,2' dihydroxy-, 4,4' di-(dimethoxymethylsilyoxyl) Benzophenone A mixture of the title compound, triethoxymethylsilane, triethoxyphenylsilane, propanol, and water is prepared via intensive mixing to yield a homogeneous solution. Dilute acetic acid in water is added to initiate the sol-gel polymerization and liberate the bound tetrahydroxybenzophenone into the polymerized matrix at a rate that is dependent of the temperature and concentrations of the reactants. A temperature of ca. 50° C. is used to facilitate the reaction. The as-reacted solution is coated onto a glass substrate using a doctor blade and cured at a temperature of ca. 220 to yield a polysiloxane film wherein the UV absorber is not covalently bonded into the matrix and is evenly distributed throughout the matrix.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A UV-radiation absorbing compound, comprising: alternating repeat units of:

(1) a first monomer derived from a compound having the general formula:

$(CH_2OCHCH_2)-R_z-[(R_a(OR)_b-Si-O-Si-R_a(OR)_b)]_c-R_z-(CH_2OCHCH_2)$ wherein $(CH_2OCHCH_2)$ is an epoxy group, $R_z$ is an organic group bonded to a siloxane silicon atom and epoxy groups, $R_a$ is an organic group bonded to a silicon atom and comprises from one to six carbon atoms, $(OR)_b$ is an alkoxy-group wherein R is an organic radical having from one to six carbon atoms, a and b are each at least one, a+b are equal to 3, and c represents the number of Si—O—Si repeat units and is at least 1, and (2) a second monomer derived from an UV-absorbing aromatic compound having at least two aromatic hydroxyl groups reactive with epoxy groups on said first monomer.

2. A UV-absorbing compound according to claim 1 wherein the second monomer is a di-, tri-, or tetrafunctional hydroxybenzophenone.

3. A UV-absorbing compound according to claim 1 wherein the second monomer is 2,2' dihydroxybenzophenone or 2,2'-4,4' tetrahydroxybenzophenone.

4. A method of preparing a UV-absorbing polymer, comprising the steps of:
   (a) providing a first monomer, the monomer being an epoxy-terminated siloxane, to a reaction vessel,
   (b) providing a second monomer, the second monomer being a UV-absorbing aromatic compound having at least two aromatic hydroxyl groups reactive with epoxy groups on said first monomer, to a reaction vessel, and
   (c) reacting said first and second monomers through epoxy and hydroxyl functions to produce a condensation product having a molecular weight of at least 400 grams per mole.

5. A method according to claim 4, wherein step (c) is practiced by reacting said first and second monomers in the presence of a coordination catalyst.

6. A method according to claim 4, wherein step (c) is practiced by reacting said first and second monomers in the presence of a tetramethyl ammonium chloride catalyst.

7. A method of preparing a UV screening siloxane film comprising the steps of
   (a) providing to a reaction vessel a quantity of a diepoxy siloxane monomer,
   (b) adding a benzophenone having at least two reactive hydroxyl groups to the reaction vessel,
   (c) reacting said diepoxy siloxane monomer and said benzophenone via a coordination catalyst to prepare a soluble UV screening polymer,
   (d) adding a portion of at least one polymerizible alkoxysilane monomer having the formula $SiR_x(OR)_y$, wherein x has the value one or two, y is 4–x, R is an organic group and (OR) is an alkoxy-group;
   (e) adding a silane reaction catalyst;
   (f) heating the mixture to prepare a substantially crosslinked siloxane;
   (g) coating the mixture onto a substrate; and
   (h) heating the coated substrate to provide a cured siloxane coated substrate.

* * * * *